United States Patent [19]

Sokukawa et al.

[11] Patent Number: 5,227,515

[45] Date of Patent: Jul. 13, 1993

[54] PROCESS FOR PRODUCING LOWER ALKYL 2-KETO-L-GULONATE

[75] Inventors: Masaki Sokukawa, Takatsuki; Yoshihiro Yasumura, Kobe; Kaoru Makino, Toyonaka, all of Japan

[73] Assignee: Takeda Chemical Industries, Ltd., Osaka, Japan

[21] Appl. No.: 953,881

[22] Filed: Sep. 30, 1992

[30] Foreign Application Priority Data

Oct. 1, 1991 [JP] Japan .................. 3-253580

[51] Int. Cl.$^5$ ............................. C07C 69/66
[52] U.S. Cl. .................................. 560/174
[58] Field of Search ........................ 560/174

[56] References Cited

U.S. PATENT DOCUMENTS

| 4,837,365 | 6/1989 | Morel | 560/174 X |
| 4,892,966 | 1/1990 | Wild | 560/174 |
| 5,118,833 | 6/1992 | Mori et al. | 560/174 X |

FOREIGN PATENT DOCUMENTS 0403993 12/1990 European Pat. Off. .

Primary Examiner—Arthur C. Prescott
Attorney, Agent, or Firm—Wenderoth, Lind & Ponack

[57] ABSTRACT

There is disclosed a process for producing lower alkyl 2-keto-L-gulonate which comprises reacting 2-keto-L-gulonic acid with a lower alcohol in the presence of an acid, and simultaneously distilling off the resulting water together with the lower alcohol while continuously introducing a lower alcohol. By using the lower alkyl 2-keto-L-gulonate thus produced, L-ascorbate can be prepared in high purity and high yield.

11 Claims, No Drawings

PROCESS FOR PRODUCING LOWER ALKYL 2-KETO-L-GULONATE

FIELD OF THE INVENTION

The present invention generally relates to a process for producing a metal L-ascorbate, more particularly, to a process for producing a lower alkyl 2-keto-L-gulonate used in the production of a metal L-ascorbate.

BACKGROUND OF THE INVENTION

Usually, a metal L-ascorbate such as sodium L-ascorbate is produced industrially as an intermediate product in the improved process for producing L-ascorbic acid, namely so-called Reichstein process [T. Reichstein and A. Grussner, Helv. Chim. Acta, 17, 311 (1943)] and is obtained from a lower alkyl 2-keto-L-gulonate such as methyl 2-keto-L-gulonate. In general, according to this process, the lower alkyl ester is obtained by esterification of diacetone-2-keto-L-gulonic acid (DAGA.H$_2$O) with a lower alcohol in the presence of sulfuric acid, and the yield of the metal L-ascorbate is limited due to equilibrium of the esterification. Then, in Reichstein process, usually heating is carried out for a relatively long period of time to increase the degree of esterification and thus attain the satisfactory degree of esterification. However, such a heating adversely influences on purity.

In order to increase purity, for example, a process wherein sodium bicarbonate is added to a reaction mixture after esterification to precipitate impurities, followed by filtration (JP-A 3-38579) has been known.

However, such a known process is accompanied by difficulties in the operation from the viewpoint of industrial production. Further, it is necessary to treat the filtrate separated again to recover the esterified product therein and it is not always an advantageous process from the economical viewpoint.

OBJECTS OF THE INVENTION

The main object of the present invention is to provide a process for producing a lower alkyl 2-keto-L-gulonate used in the production of a metal L-ascorbate.

This object as well as other objects and advantages of the present invention will become apparent to those skilled in the art from the following description.

SUMMARY OF THE INVENTION

Under these circumstances, the present inventors have intensively studied to develop an improved process for producing a lower alkyl 2-keto-L-gulonate which is superior in yield, costs and the like. As a result, it has been found that, when 2-keto-L-gulonic acid is esterified with a lower alcohol, removal of water formed during this esterification from a reaction system is a useful means for shifting equilibrium of the esterification in the direction of formation of the ester product and thereby the desired product can be obtained in purity of about 97% or higher and yield of about 94% or higher. Thus, the present invention has been completed.

That is, according to the present invention, there is provided a process for producing a lower alkyl 2-keto-L-gulonate which comprises reacting 2-keto-L-gulonic acid with a lower alcohol in the presence of an acid, and simultaneously distilling off the resulting water together with the lower alcohol while continuously introducing a lower alcohol.

DETAILED DESCRIPTION OF THE INVENTION

In the present invention, since 2-keto-L-gulonic acid monohydrate (2KGA.H$_2$O) is used as the starting material, a lower alkyl ester of 2-keto-L-gulonic acid and 2 molecules of water are produced. To remove the water, a lower alcohol is continuously introduced into a reaction system.

The following scheme shows the reactions.

Reichstein process:

Present Invention:

wherein R is lower alkyl.

As the acid used as a catalyst in the present invention, there are mineral acids. Examples thereof include sulfuric acid, hydrochloric acid, phosphoric acid and the like. In particular, sulfuric acid is preferred. The amount of the acid to be used is 0.0054 to 0.0162 mol, preferably 0.0054 to 0.011 mol per 1 mol of 2-keto-L-gulonic acid.

As the lower alcohol to be used in the present invention, there are those having 1 to 4 carbon atoms such as methanol, ethanol and the like. In particular, methanol is preferred.

In the process of the present invention, firstly, the lower alcohol in an amount of 4 to 7 mol per 1 mol of 2-keto-L-gulonic acid is placed in a reaction system and the esterification is started. Then, the resulting water is distilled off together with the lower alcohol while the lower alcohol in the same amount as that of the distilled lower alcohol is continuously introduced into the reaction system. The lower alcohol to be introduced may be liquid or vapor. The amount of the lower alcohol to be introduced is 40 to 60 mol, preferably 50 to 60 mol per 1 mol of 2-keto-L-gulonic acid.

Thus, according to the process of the present invention, 2-keto-L-gulonic acid is esterified by the catalytic activity of the acid to give the lower alkyl ester of 2-keto-L-gulonic acid. The water formed is distilled off together with the lower alcohol. Normally, the mixture of the distilled water and the lower alcohol is separated into water and the lower alcohol and they are recovered in a pressurized fractionating column. In this case, it is preferred that vapor of the distilled lower alcohol from the top of the pressurized fractionating column is continuously and directly introduced into the reaction system to use the lower alcohol for removal of water formed because formation of the esterified product is promoted, the lower alcohol is utilized efficiently and heat is saved.

The reaction temperature during esterification is normally 67° to 71° C. Normally, the reaction is completed within 5 to 6 hours. Normally, crystals of the ester deposit because of its solubility.

The 2-keto-L-gulonic acid used as the starting material in the present invention can be prepared by a known method. For example, it can be prepared by oxidation of L-sorbose according to a known method.

The lower alkyl 2-keto-L-gulonate thus obtained can be used for the production of a metal L-ascorbate according to a known method.

For example, after completion of esterification, total reflux is carried out. Then, 7 mol of a lower alcohol per 1 mol of 2-keto-L-gulonic acid is added under reflux of lower alcohol, followed by addition of an alkali/alcohol solution (10%) to be used in the next lactonization to dissolve the ester.

The alkali/alcohol solution is continuously added to the ester solution under reflux of the lower alcohol, and lactonization is carried out to obtain a metal L-ascorbate.

As the metal of the metal L-ascorbate, there are, for example, alkali metals (e.g., sodium, potassium, etc.), alkaline earth metals (e.g., calcium, magnesium, etc.) and the like.

In the production of the metal L-ascorbate, as the alkali, there can be used a hydroxide or bicarbonate of the above metal. Preferably, it is sodium hydroxide, potassium hydroxide, more preferably sodium hydroxide. In this case, the alkali concentration is preferably 11.0 to 11.2% by weight.

When the above alkali/alcohol solution is continuously added, the lower alkyl ester is lactonized to obtain the desired product. Normally, after about 1 hour from initiation of the reaction, crystals deposit. When the pH becomes 9.0±0.2, the addition of the alkali/alcohol solution is stopped.

The lactonization is completed within about 2 hours. After completion of the reaction, the reaction mixture is cooled to room temperature with stirring to obtain the precipitate of the metal L-ascorbate.

For separation of the precipitate, any solid/liquid separation method such as filtration, centrifugation or the like can be adopted.

According to the process of the present invention, by introducing vapor of a lower alcohol directly into the esterification reaction system, energy for the esterification can be saved, and a metal L-ascorbate can be prepared in purity of about 97% or higher and yield of about 94% or higher. This yield is higher by about 1.5% than that obtained by conventional methods.

The following examples further illustrate the present invention in detail but are not to be construed to limit the scope thereof. In the examples, all the percents are by weight unless otherwise stated.

EXAMPLE 1

2-Keto-L-gulonic acid (content: 89.75%, water: 8.69%) (160 g), methanol (210 ml) and conc. sulfuric acid (0.8 g) were introduced into a 1 liter flask. The mixture was warmed with stirring. When the inner temperature reached 66° C., distillation of methanol was started. At the same time, introduction of liquid methanol in the same amount as that of distilled methanol into the flask was started with a constant delivery pump. The methanol was distilled off in an amount of 300 ml per hour (the amount of methanol to be introduced was also 300 ml per hour). After 3 hours, crystals of methyl 2-keto-L-gulonate began to deposit.

After 6 hours, the esterification was completed. The amount of the methanol introduced (distilled off) was 1,800 ml. Water content in the distilled methanol was 1.88%. The value showed that 97.5% of the total amount of water produced in the reaction system and water already present was distilled off (hereinafter referred to as dehydration rate). Then, total reflux was carried out, and methanol (210 ml) was introduced. And, a solution (14 ml) of granular sodium hydroxide (50.16 g) dissolved in methanol (500 ml) was introduced to dissolve the crystals of methyl 2-keto-L-gulonate. Introduction of the sodium hydroxide/methanol solution was continued. After about 30 minutes, the reaction mixture became cloudy, and deposition of crystals of sodium L-ascorbate was observed. When the pH of the reaction mixture reached 9.2, the lactonization was completed. The reaction time was 2 hours. The amount of the sodium hydroxide/methanol solution consumed was 310 ml.

The reaction mixture was cooled with stirring. When the temperature reached room temperature, the mixture was filtered in vacuo by using a glass filter. The wet crystals were dried under reduced pressure at 40° C. for 1 hour and at room temperature for 12 hours. The crystals thus obtained were determined by high performance liquid chromatography (HPLC). As a result, it was found that sodium L-ascorbate (142.5 g, purity: 97.9%) was present (yield: 95.1%), while sodium 2-keto-L-gulonate (1.72%) remained.

HPLC was carried out under the following conditions. The same conditions were used in the other examples hereinafter.

| Column: | Biorad, HPX-87H |
|---|---|
| Mobile phase: | 0.1M Ammonium sulfate |
| Detection: | Differential refractometer |

EXAMPLE 2

2-Keto-L-gulonic acid (content: 89.75%, water: 8.69%) (160 g), methanol (210 ml) and conc. sulfuric acid (0.8 g) were introduced into a 1 liter flask. The mixture was warmed with stirring. When the inner temperature reached 66° C., distillation of methanol was started. At the same time, introduction of liquid methanol in the same amount as that of distilled methanol into the flask was started with a constant delivery pump. The methanol was distilled off in an amount of 300 ml per hour (the amount of methanol to be introduced is also 300 ml per hour). After 3 hours, crystals of methyl 2-keto-L-gulonate began to deposit.

After 5 hours, the esterification was completed. The amount of the methanol introduced (distilled off) was 1,500 ml. Water content in the distilled methanol was 2.01%. The dehydration rate was 86.7%.

Then, total reflux was carried out and methanol (210 ml) was introduced. Then, a solution (14 ml) of granular sodium hydroxide (50.16 g) dissolved in methanol (500 ml) was introduced to dissolve the crystals of methyl 2-keto-L-gulonate. Introduction of the sodium hydroxide/methanol solution was continued. After about 30 minutes, the reaction mixture became cloudy and deposition of crystals of sodium L-ascorbate was observed. When the pH of the reaction mixture reached 9.2, the lactonization was completed. The reaction time was 2 hours. The amount of the sodium hydroxide/methanol solution consumed was 306 ml.

The reaction mixture was cooled with stirring. When the temperature reached room temperature, the mixture was filtered in vacuo by using a glass filter. The wet crystals were dried under reduced pressure at 40° C. for 1 hour and at room temperature for 12 hours. The crystals thus obtained were determined by HPLC. As a result, it was found that sodium L-ascorbate (142.2 g, purity: 95.7%) was present (yield: 92.9%), while sodium 2-keto-L-gulonate (2.75%) remained.

EXAMPLE 3

2-Keto-L-gulonic acid (content: 89.75%, water: 8.69%) (160 g), methanol (120 ml) and conc. sulfuric acid (0.8 g) were introduced into a 1 liter flask. The mixture was warmed with stirring. When the inner temperature reached 66° C., distillation of methanol was started. At the same time, introduction of liquid methanol in the same amount as that of distilled methanol into the flask was started with a constant delivery pump. The methanol was distilled off in an amount of 300 ml per hour (the amount of methanol to be introduced is also 300 ml per hour). After 3 hours, crystals of methyl 2-keto-L-gulonate began to deposit.

After 6 hours, the esterification was completed. The amount of the methanol introduced (distilled off) was 1,800 ml. Water content in the distilled methanol was 1.97%. The dehydration rate was 100%.

Then, total reflux was carried out, and methanol (210 ml) was introduced. Then, a solution (14 ml) of granular sodium hydroxide (50.16 g) dissolved in methanol (500 ml) was introduced to dissolve the crystals of methyl 2-keto-L-gulonate. Introduction of the sodium hydroxide/methanol solution was continued. After about 30 minutes, the reaction mixture became cloudy, and deposition of crystals of sodium L-ascorbate was observed. When the pH of the reaction mixture reached 9.2, the lactonization was completed. The reaction time was 2 hours. The amount of the consumed sodium hydroxide/methanol solution was 311 ml.

The reaction mixture was cooled with stirring. When the temperature reached room temperature, the mixture was filtered in vacuo by using a glass filter. The wet crystals were dried under reduced pressure at 40° C. for 1 hour and at room temperature for 12 hours. The crystals thus obtained were determined by HPLC. As a result, it was found that sodium L-ascorbate (140.9 g, purity: 97.6%) was remained.

EXAMPLE 4

2-Keto-L-gulonic acid (content: 90.7%, water: 8.57%) (160 g), methanol (210 ml) and conc. sulfuric acid (0.6 g) were introduced into a 1 liter flask. The mixture was warmed with stirring. When the inner temperature reached 66° C., distillation of methanol was started. At the same time, introduction of liquid methanol in the same amount as that of distilled methanol to the flask was started with a constant delivery pump. The methanol was distilled off in an amount of 300 ml per hour (the amount of methanol to be introduced is also 300 ml per hour). After 3 hours, crystals of methyl 2-keto-L-gulonate began to deposit.

After 6 hours, the esterification was completed. The amount of the methanol introduced (distilled off) was 800 ml. Water content in the distilled methanol was 1.92%. The dehydration rate was 94.2%.

Then, total reflux was carried out and methanol (210 ml) was introduced. Then, a solution (14 ml) of granular sodium hydroxide (50.16 g) dissolved in methanol (500 ml) was introduced to dissolve the crystals of methyl 2-keto-L-gulonate. Introduction of the sodium hydroxide/methanol solution was continued. After about 30 minutes, the reaction mixture became cloudy, and deposition of crystals of sodium L-ascorbate was observed. When the pH of the reaction mixture reached 9.2, the lactonization was completed. The reaction time was 2 hours. The amount of the sodium hydroxide/methanol solution consumed was 306 ml.

The reaction mixture was cooled with stirring. When the temperature reached room temperature, the mixture was filtered in vacuo by using a glass filter. The wet crystals were dried under reduced pressure at 40° C. for 1 hour and at room temperature for 12 hours. The crystals thus obtained were determined by HPLC. As a result, it was found that sodium L-ascorbate (144.03 g, purity: 97.4%) was present (yield: 94.7%), while sodium 2-keto-L-gulonate (2.49%) remained.

EXAMPLE 5

2-Keto-L-gulonic acid (content: 90.7%, water: 8.57%) (160 g), methanol (120 ml) and conc. sulfuric acid (0.4 g) were introduced to a 1 liter flask. The mixture was warmed with stirring. When the inner temperature reached 66° C., distillation of methanol was started. At the same time, introduction of liquid methanol in the same amount as that of distilled methanol into the flask was started with a constant delivery pump. The methanol was distilled off in an amount of 300 ml per hour (the amount of methanol to be introduced is also 300 ml per hour). After 3 hours, crystals of methyl 2-keto-L-gulonate began to deposit.

After 6 hours, the esterification was completed. The amount of the methanol introduced (distilled off) was 1,800 ml. Water content in the distilled methanol was 1.85%. The dehydration rate was 93.5%.

Then, total reflux was carried out, and methanol (210 ml) was introduced. Then, a solution (14 ml) of granular sodium hydroxide (50.16 g) dissolved in methanol (500 ml) was introduced to dissolve the crystals of methyl 2-keto-L-gulonate. Introduction of the sodium hydroxide/methanol solution was continued. After about 30 minutes, the reaction mixture became cloudy, and deposition of crystals of sodium L-ascorbate was observed. When the pH of the reaction mixture reached 9.2, the lactonization was completed. The reaction time was 2 hours. The amount of the consumed sodium hydroxide/methanol solution was 311 ml.

The reaction mixture was cooled with stirring. When the temperature reached room temperature, the mixture was filtered in vacuo by using a glass filter. The wet crystals were dried under reduced pressure at 40° C. for 1 hour and at room temperature for 12 hours. The crystals thus obtained were determined by HPLC. As a result, it was found that sodium L-ascorbate (143.35 g, purity: 96.1%) was present (yield: 93.5%), while sodium 2-keto-L-gulonate (2.0%) remained.

EXAMPLE 6

2-Keto-L-gulonic acid (content: 100%, water: 0%) (160 g), methanol (210 ml) and conc. sulfuric acid (0.8 g) were introduced to a 1 liter flask. The mixture was warmed with stirring. When the inner temperature reached 66° C., distillation of methanol was started. At the same time, introduction of liquid methanol in the same amount as that of distilled methanol to the flask was started with a constant delivery pump. The methanol was distilled off in an amount of 300 ml per hour (the amount of methanol to be introduced is also 300 ml per hour). After 3 hours, crystals of methyl 2-keto-L-gulonate began to deposit.

After 4 hours, the esterification was completed. The amount of the methanol introduced (distilled off) was 1,200 ml. Water content in the distilled methanol was 1.53%. The dehydration rate was 100%.

Then, total reflux was carried out, and methanol (210 ml) was introduced. Then, a solution (14 ml) of granular sodium hydroxide (50.16 g) dissolved in methanol (500 ml) was introduced to dissolve the crystals of methyl 2-keto-L-gulonate. Introduction of the sodium hydroxide/methanol solution was continued. After about 30 minutes, the reaction mixture became cloudy, and deposition of crystals of sodium L-ascorbate was observed. When the pH of the reaction mixture reached 9.2, the lactonization was completed. The reaction time was 2 hours. The amount of the consumed sodium hydroxide/methanol solution was 306 ml.

The reaction mixture was cooled with stirring. When the temperature reached room temperature, the mixture was filtered in vacuo by using a glass filter. The wet crystals were dried under reduced pressure at 40° C. for 1 hour and at room temperature for 12 hours. The crystals thus obtained were determined by HPLC. As a result, it was found that sodium L-ascorbate (158.95 g, purity: 97.2%) was present (yield: 94.6%), while sodium 2-keto-L-gulonate (2.2%) remained.

EXAMPLE 7

2-Keto-L-gulonic acid (content: 90.0%, water: 8.3%) (16 kg), methanol (21 liters) and conc. sulfuric acid (80 g) were introduced to a 100 liter reactor having a jacket. The mixture was warmed by the jacket with stirring. When the inner temperature reached 66° C., distillation of methanol was started. At the same time, liquid methanol in the same amount as that of distilled methanol was introduced into a heater with a constant delivery pump. The liquid methanol became vapor in the heater and then it was introduced into the reactor. The methanol was distilled off in an amount of 30 liters per hour (the amount of methanol to be introduced is also 30 liters per hour). After 3 hours, crystals of methyl 2-keto-L-gulonate began to deposit.

After 6 hours, the esterification was completed. The amount of the methanol introduced (distilled off) was 180 liters.

Then, total reflux was carried out, and methanol (21 liters) was introduced. And, a solution (1.4 liters) of granular sodium hydroxide (5.016 kg) dissolved in methanol (50 liters) was introduced to dissolve the crystals of methyl 2-keto-L-gulonate. Introduction of the sodium hydroxide/methanol solution was continued. After about 30 minutes, the reaction mixture became be cloudy and deposition of crystals of sodium L-ascorbate was observed. When the pH of the reaction mixture reached 9.2, the lactonization was completed. The reaction time was 2 hours. The amount of the consumed sodium hydroxide/methanol solution was 31.0 liters.

The reaction mixture was cooled with stirring. When the temperature reached room temperature, the mixture was filtered with a centrifugal separator. The wet crystals were dried under reduced pressure at 40° C. for 1 hour and at room temperature for 12 hours. The crystals thus obtained were determined by HPLC. As a result, it was found that sodium L-ascorbate (14.32 kg, purity: 95.7%) was present (yield: 93.3%), while sodium 2-keto-L-gulonate (1.6%) remained.

EXAMPLE 8

2-Keto-L-gulonic acid (content: 89.24%, water: 8.7%) (200 kg), methanol (300 liters) and conc. sulfuric acid (0.75 kg) were introduced into a 2,000 liter reactor having a jacket. The mixture was warmed by the jacket with stirring. When the inner temperature reached 66° C., distillation of methanol was started. At the same time, liquid methanol in the same amount as that of distilled methanol was introduced into a heater with a constant delivery pump. The liquid methanol became vapor in the heater and then it was introduced into the reactor. The methanol was distilled off in an amount of 352 liters per hour (the amount of methanol to be introduced is also 352 liters per hour). After 3 hours, crystals of methyl 2-keto-L-gulonate began to deposit.

After 9 hours, the esterification was completed. The amount of the methanol introduced (distilled off) was 3,170 liters.

Then, total reflux was carried out, and methanol (300 liters) was introduced. Then, a solution (35 liters) of granular sodium hydroxide (38.9 kg) dissolved in methanol (320 liters) was introduced to dissolve the crystals of methyl 2-keto-L-gulonate. Introduction of the sodium hydroxide/methanol solution was continued. After about 30 minutes, the reaction mixture became cloudy, and deposition of crystals of sodium L-ascorbate was observed. When the pH of the reaction mixture reached 9.2, the lactonization was completed. The reaction time was 2 hours.

The reaction mixture was cooled with stirring. When the temperature reached room temperature, the mixture was filtered with a centrifugal separator. The wet crystals were dried under reduced pressure at 40° C. for 1 hour and at room temperature for 12 hours. The crystals thus obtained sodium L-ascorbate (179.88 kg, purity: 95.8%) was present (yield: 94.6%), while sodium 2-keto-L-gulonate (2.5%) remained.

What is claimed is:

1. A process for producing a lower alkyl 2-keto-L-gulonate which comprises reacting 2-keto-L-gulonic acid with a lower alcohol in the presence of an acid, and simultaneously distilling off the resulting water together with the lower alcohol while continuously introducing a lower alcohol.

2. A process according to claim 1, wherein 2-keto-L-gulonic acid is its monohydrate.

3. A process according to claim 1, wherein the lower alcohol is an alcohol having 1 to 4 carbon atoms.

4. A process according to claim 3, wherein the lower alcohol is methanol.

5. A process according to claim 4, wherein the lower alcohol introduced continuously is vapor of methanol.

6. A process according to claim 1, wherein the distilled lower alcohol is separated and introduced into a reaction system.

7. A process according to claim 1, wherein the acid is a mineral acid.

8. A process according to claim 7, wherein the mineral acid is sulfuric acid.

9. A process according to claim 1, wherein the amount of the acid is 0.0054 to 0.0162 mol per 1 mol of 2-keto-L-gulonic acid.

10. A process according to claim 1, wherein the amount of the lower alcohol to be introduced is 40 to 60 mol per 1 mol of 2-keto-L-gulonic acid.

11. A process according to claim 1, wherein the lower alkyl 2-keto-L-gulonate produced is methyl 2-keto-L-gulonate.

* * * * *